(12) United States Patent
Lalonde

(10) Patent No.: US 6,315,780 B1
(45) Date of Patent: Nov. 13, 2001

(54) BONE CLAMP FOR DYNAMIC AND NON-DYNAMIC COMPRESSION OF TRANSVERSE FRACTURES AND METHOD OF USE THEREOF

(75) Inventor: Donald H. Lalonde, Saint John (CA)

(73) Assignee: Accurate Surgical & Scientific Instruments Corporation, Westbury, NY (US)

( * ) Notice: Subject to any disclaimer, the term of this patent is extended or adjusted under 35 U.S.C. 154(b) by 0 days.

(21) Appl. No.: 09/290,644

(22) Filed: Apr. 12, 1999

(51) Int. Cl.⁷ .................................................. A61B 17/28
(52) U.S. Cl. ............................ 606/86; 606/105; 606/207
(58) Field of Search ................................ 606/207, 205, 606/206, 208, 151, 158, 120, 163, 96–98, 86–90, 102, 105; 128/18–20

(56) References Cited

U.S. PATENT DOCUMENTS

| | | |
|---|---|---|
| Re. 31,628 | 7/1984 | Allgower et al. . |
| 2,583,896 * | 1/1952 | Siebrandt ............................... 606/86 |
| 3,552,389 | 1/1971 | Allgower et al. . |
| 3,668,972 | 6/1972 | Allgower et al. . |
| 3,746,002 * | 7/1973 | Haller ................................... 606/207 |
| 3,828,791 | 8/1974 | Santos . |
| 4,219,015 | 8/1980 | Steinemann . |
| 4,484,570 | 11/1984 | Sutter et al. . |
| 4,493,317 | 1/1985 | Klaue . |
| 4,513,744 | 4/1985 | Klaue . |
| 4,599,999 | 7/1986 | Klaue . |
| 4,723,548 | 2/1988 | Lalonde . |
| 4,848,338 | 7/1989 | De Satnick et al. . |
| 4,867,139 * | 9/1989 | Girzadas ............................... 128/20 |
| 4,944,739 | 7/1990 | Torre . |

(List continued on next page.)

FOREIGN PATENT DOCUMENTS 856-450     8/1981   (SU) .
1082-412    3/1984   (SU) .

OTHER PUBLICATIONS

Manual of Small Animal Fracture Repair and Management. Principles of Fracture Surgery, pp. 79–82.
Leibinger Catalog Page Showing Item 64–01100—date unknown.
Link Instrumentation for Hand Surgery Catalog, pp. 69 and 80–83—date unknown.
KMedic Brochure, 4 sheets—date unknown.
Catalog, P. 66 and unknown page, on Lowman clamp and Backhaus claimp—source and date unknown.
Codman Catalog, PP. 208–209, date unknown.
Cover and pp. 356 and 357 of Miltex Surgical Instruments Catalog—date unknown.

*Primary Examiner*—Cary E. O'Connor
(74) *Attorney, Agent, or Firm*—Jordan and Hamburg LLP (57) ABSTRACT

A bone clamp permits temporary securement of adjacent bone segments of an involved bone separated by a fracture following open reduction thereof. A pair of jaw members opposed to one another are mutually urgeable together, each of the pair of jaw members including gripping structure carried on a support for fixedly engaging the abutted segments of the involved bone, the fracture being oriented within an intermediate region located between said opposed ends of the support. In an embodiment directed to non-dynamic compression of the fracture, the gripping structure either fictionally engages the surface of the bone, or penetrates perpendicular to a longitudinal bone axis. An alternative embodiment is directed to a dynamic compression clamp, in which the gripping structure includes piercing structure which enters respective bone segments at an opposed angle to the fracture, and in which penetrating movement of the piercing structure thereby effects an urging together of the bone segments in a direction of the fracture line. Such temporary securement permits subsequent repair of the fracture by a desired fixation process.

9 Claims, 4 Drawing Sheets

U.S. PATENT DOCUMENTS

| | | |
|---|---|---|
| 4,997,434 | 3/1991 | Seedhom et al. . |
| 5,133,715 | 7/1992 | Lenzo . |
| 5,133,724 * | 7/1992 | Wilson, Jr. et al. ................. 606/207 |
| 5,370,646 | 12/1994 | Reese et al. . |
| 5,578,032 * | 11/1996 | Lalonde ............................... 606/207 |
| 5,690,640 | 11/1997 | Gotfried . |
| 5,697,933 * | 12/1997 | Gundlapalli et al. .................. 606/96 |
| 5,797,919 * | 8/1998 | Brinson ................................ 606/105 |
| 5,814,067 | 9/1998 | Fleischmann . |
| 6,007,552 * | 12/1999 | Fogarty et al. ...................... 606/157 |

* cited by examiner

BONE CLAMP FOR DYNAMIC AND NON-DYNAMIC COMPRESSION OF TRANSVERSE FRACTURES AND METHOD OF USE THEREOF

BACKGROUND OF THE INVENTION

The present invention relates to a bone clamp used in surgical procedures for repair of bone fractures requiring fixation for the proper mending thereof, and more particularly, to a bone clamp for use in compression of transverse fractures for subsequent fixation by suitable means while retained in abutted contact following open reduction of the fracture.

A variety of bone clamps are commercially available for reducing bone fractures, i.e. the process of urging fractured portions of a bone into proper alignment with one another. Generally falling into two categories, bone clamps include parallel and perpendicular types, designated in accordance with the orientation of the axis of the device with respect to the axis of the fracture. A parallel bone clamp approaches the axis of the fracture parallel with its own axis. A perpendicular bone clamp approaches the axis of the fracture with its own axis perpendicular to the axis of the fracture.

Included among the more commonly used parallel bone clamps are the Verbrugge, the Lange, the Kern, the Ulrich, the Lambotte, the Seidel, and the Lanenbeck. Each of these clamping devices utilizes a ratchet mechanism to apply and maintain pressure on the severed portions of the bone being urged into mutual contact alignment.

In addition to the aforementioned clamps specifically designed for reduction procedures, surgeons have for many years routinely relied upon the common towel clip to reduce fractures and effect repair of bone fractures, in particular where small bones were involved. Deriving its name from its originally designed purpose of holding towels together in a sterile field, the towel clip was never expressly intended for use in bone fracture surgery. When applied to use as a bone repair device, the towel clip falls into the category of the aforementioned parallel type bone clamps, its shape resembling a pair of miniature ice tongs having a pair of sharp, opposing points which may be brought together by scissor action, and which serve to securely grip the bone from opposed sides thereof. A ratchet mechanism assists in applying pressure on a fractured bone interposed between the points, and maintains pressure on the bone without requiring continued manipulation thereof by the user. The towel clip has found application as a device used in small bone reductions because it occupies less space than most parallel bone clamps. In addition, its rugged design permits the application of relatively large forces required to reduce bones and the two sharp points reliably grasp the opposed bone surfaces without slipping. Its design, however, is not adapted to use in circumstances in which a transverse fracture separates the bone segments requiring reduction and securement for subsequent fixation, since gripping by the towel clip relies upon single points positioned in direct opposition from one another across the longitudinal direction of the involved bone.

A bone clamp is proposed in U.S. Pat. No. 5,578,032 entitled "Bone Clamp", and issued to Lalonde on Nov. 26, 1996 having structure falling into the aforementioned perpendicular bone clamp category, and in accordance with which the instrument is inserted into the wound crosswise to the fractured bone. Its special configuration is uniquely adapted, in particular, for use in repairing small fractures. The disclosed bone clamp includes a pair of clamps extending perpendicular to a ratcheted scissor portion. The clamps, each having one or more sharp points at an end thereof, may be urged together by operation of the scissor portion, thereby contacting opposed sides of a bone positioned therebetween. Since the aforementioned clamp provides only a single pair of opposed points, or plural points spaced apart on each clamp only a minimal distance from one another, the design is exclusively suited for repair of oblique fractures, wherein the fracture line runs crosswise between a compression axis of the opposed clamps brought into engagement with the bone segments, and does not offer a satisfactory solution to the problem of open reduction of transverse fractures.

Also disclosed in the above Lalonde patent is an embodiment directed to a device comprised of two bone clamps mounted on a slide bar to permit approximation of the bone clamps, each gripping a separated bone segment. Continued approximation of the clamps one to the other results in reduction of the bone segments and permits subsequent fixation by accepted methods.

In addition to the aforementioned non-dynamic compression devices in which the reduced bones segments are maintained in aligned contact without application of any additionally applied axially compressive forces, a device is described in the prior art which permits dynamic compression of the fracture for better engagement of abutted ends of the adjacent bone segments, thought to result in improved healing and recovery. The known device, a type of bone plate which acts as an internal splint while the bone heals, is affixed to the bone in a position spanning the fracture site. The bone plate is generally contoured to conform to the shape of the bone, and is fixed in place by the use of screws which self-tap into the bone. To provide dynamic compression, the specialized bone plate, the structural and operational aspects of which are described for example in "Manual of Small Animal Fracture Repair and Management", pages 80–81, and which is incorporated herein by reference, includes holes within which screws, received therethrough and into respective aligned bone segments, can slide axially. The holes are provided with eccentrically configured shoulders which impart sliding motion to the screws as they are tightened, which in turn results in axial movement also of the bones into compressive abutted engagement. Although quite effective in achieving dynamic compression, use of such plates does not allow a surgeon the option of using other fixation methods, and further requires separate use of a bone clamp to maintain alignment while applying such plate.

A clamp design would therefore be desirable by means of which a reduced transverse fracture could be immobilized to permit fixation by a desired method prior to removal of the clamp, and which could advantageously provide dynamic compression attendant a clamping operation whereby subsequent fixation which would not necessarily be limited to use of a bone plate.

Accordingly, it is an object of the invention to provide a bone clamp which overcomes the drawbacks of the prior art.

It is a further object of the invention to provide a bone clamp which may be inserted into a surgical incision for maintaining bone segments separated by a transverse fracture in a reduced state to permit subsequent fixation thereof.

It is a still further object of the invention to provide such bone clamp in a form utilizing a ratchet mechanism for simple and efficient operation, and which thereby permits hands-free maintenance of the clamped positioning of the fracture during subsequent mending thereof.

It is yet a further object of the invention to provide a bone clamp which may be used to provide dynamic compression of a fractured bone following reduction of the bone segments and subsequently maintaining axially compressive alignment for fixation by a desired method.

It is yet a further object of the invention to provide a bone clamp of the above type which is economical, yet rugged enough to withstand the forces of bone reduction.

SUMMARY OF THE INVENTION

Briefly stated, there is provided a bone clamp which permits temporary securement of adjacent bone segments of an involved bone separated by a fracture following open reduction thereof. A pair of jaw members opposed to one another are mutually urgeable together, each of the pair of jaw members including gripping structure carried on a support for fixedly engaging the abutted segments of the involved bone, the fracture being oriented within an intermediate region located between said opposed ends of the support. In an embodiment directed to non-dynamic compression of the fracture, the gripping structure either frictionally engages the surface of the bone, or penetrates perpendicular to a longitudinal bone axis. An alternative embodiment is directed to a dynamic compression clamp, in which the gripping structure includes piercing structure which enters respective bone segments at an opposed angle to the fracture, and in which penetrating movement of the piercing structure thereby effects an urging together of the bone segments in a direction of the fracture line. Such temporary securement permits subsequent repair of the fracture by a desired fixation process.

In accordance with these and other objects of the invention there is provided a bone clamp jaw for providing non-dynamic or dynamic compression and a method of use thereof.

In an embodiment directed to non-dynamic compression, a pair of jaws each includes support structure having an expanded dimension extending along a longitudinal axis of a bone placed therebetween, and presenting gripping structure, provided for example in the form of one or more spikes disposed on either side of each jaw in the expanded direction. During a clamping operation, a fractured bone is interposed between confronting upper and lower jaws, advantageously positioned such that a transverse fracture line lies within an intermediate region of the expanded dimension of the jaws. In such bone clamp which does not provide dynamic compression, alternative to the use of spikes, the gripping structure may comprise a roughened contact surface, one or a series of ridges or other projections for making single or multiple point contact, teeth, and any other configuration, combination of structures and/or material characteristic which achieves a frictional or penetrating grip when brought into contact with a bone interposed between opposed upper and lower jaws of the bone clamp.

In an alternative embodiment directed to a clamp providing dynamic compression of a transverse fracture, a jaw structure having support structure generally in accordance with the non-dynamic compression embodiment includes piercing structure, for example, in the form one or more spikes laterally disposed on either side of the intermediate region between ends of the jaws in the extended direction. The spikes are disposed at an angle outwardly divergent from a compression axis representative of a direction of jaw movement effected by closure of jaws during a clamping operation, and being respectively angled away from a transverse fracture line in a direction along a longitudinal axis of a bone interposed between the jaws. Prior to clamping, the bone segments are reduced, bringing them into approximate alignment. When subsequently clamped, the spikes angularly penetrate the bone segments and drive the bone segments together into dynamic compression with one another, permitting such axial compression to be maintained following removal of the clamp by fixation of the bone segments while clamped using accepted techniques such as by use of interosseous wires, K-wires, plates, screws, etc..

A method for using such dynamic compression clamp advantageously permits concomitant axial compression of a transverse fracture and temporary clamped securement permitting subsequent repair by any accepted method of fixation preferred by a surgeon.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
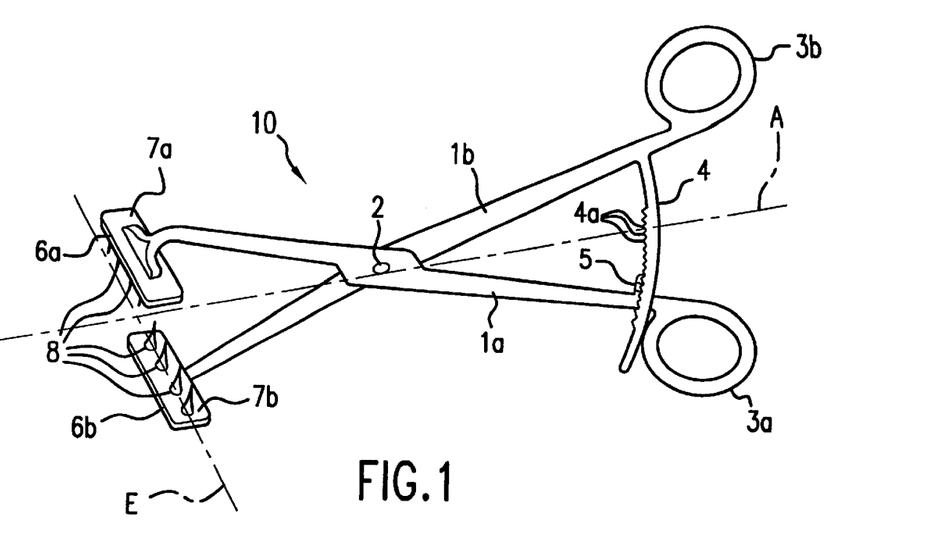
FIG. 1 is a perspective view of a bone clamp in accordance with an embodiment of the present invention utilizing parallel structure.

Referring now to FIG. 1, there is shown, generally at 10, a bone clamp, in accordance with the invention. The components of bone clamp 10 are constructed of a suitable material typically used for instruments of similar application. Generally, such materials will allow sterilization, resist corrosion, and possess good strength characteristics, such as, for example, stainless steel.

In the depicted embodiment, the bone clamp 10 is provided in the form of a parallel type clamp resembling a towel clip in overall appearance and manual operation. Bone clamp 10 includes a pair of scissor arms 1a and 1b connected through a scissor pivot 2. Finger loops 3a and 3b are provided at respective ends of scissor arms 1a and 1b for transmission of a hand motion to scissor arms 1a and 1b. Closure of bone clamp 10 is effected by urging together finger loops 3a and 3b and scissor arms 1a and 1b move to a position in which each approximates a common longitudinal scissor axis A. Finger loops 3a and 3b are advantageously closed loops, as shown, to permit opening of bone clamp 10 by movement increasing the distance between finger loops 3a and 3b in which fingers of the user are captively supported. Bone clamp 10 in FIG. 1 is shown in an open position. A ratchet arc 4 extends from one of the scissor arms 1a and 1b, for example scissor arm 1b in the depicted example, substantially along a common plane of bone clamp 10, oriented to cooperate with a corresponding ratchet cog 5 on scissor arm 1a. Ratchet arc 4 comprises a series of teeth 4a, each having a face perpendicular to ratchet arc 4 on a side facing finger loop 3b, and a sloped face on a remaining side, pursuant to conventional design. Ratchet cog 5 comprises a single tooth having a profile similar to teeth 4a, the perpendicular face of which faces finger loop 3a. This configuration allows stepwise closure of scissor arms 1a and 1b as ratchet cog 5 slips over the sloped surface of each of teeth 4a on ratchet arm 4, while the perpendicular surfaces on both ratchet cog 5 and teeth 4a engage to prevent opening of scissor arms 1a and 1b. Opening of bone clamp 10 is accomplished by a twisting action sufficient to move each of scissor arms 1a and 1b in directions away from one another and out of the common plane of bone clamp 10, thereby disengaging ratchet cog 5 from teeth 4a. As noted above, although ratchet arm 4 is shown extending from scissor arm 1b in the preferred embodiment, it could instead be made integral with scissor arm 1a, and ratchet cog 5 be relocated on scissor arm 1b. In addition, scissor arm 1b is shown crossing over scissor arm 1a, but this may be reversed, for example in the case where the instrument is to be operated by a left-handed person, facilitating release of the ratchet mechanism.

A pair of jaws 6a an d 6b are each carried at an end of a corresponding one of scissor arms 1a and 1b. Jaws 6a and 6b include support structure, which in the depicted example is conveniently provided in the form of support bars 7a and 7b, each presenting opposed gripping structure, for example, in the form of spaced-apart spikes 8 in the present embodiment, for contacting a bone (not shown) disposed therebetween when jaws 6a and 6b are urged together by user manipulation of scissor arms 1a and 1b. Support bars 7a and 7b present an expanded dimension extending between opposed ends thereof aligned with a jaw axis E, as shown in FIG. 1, to enable contact over a suitable length of a bone received between jaws 6a and 6b oriented with a longitudinal direction thereof codirectional with jaw axis E in order to thereby reliably maintain stability of the clamped union. In the depicted example of FIG. 1, jaw axis is arranged perpendicular with scissor axis A. Other angular orientations, however, as may be demanded by particular applications, are also contemplated within the scope of the invention.

The features and advantages of the present invention are realized by specialized jaw structure which may be carried on any number of clamp mechanisms, and therefore the precise mode of mechanical implementation within the contemplated scope of the invention is not restricted to a particular clamp design, such as, for example, the parallel towel clamp configuration disclosed above with reference to FIG. 1. For example, turning now to FIG. 2, an alternatively designed bone clamp is depicted, generally designated 20, which incorporates the jaw structure of the present invention used in conjunction with a perpendicular clamp configuration provided in accordance with the design guidelines disclosed in U.S. Pat. No. 5,578,032 entitled "Bone Clamp", and issued to Lalonde on Nov. 26, 1996, and which is incorporated herein by reference.

Figure 2:
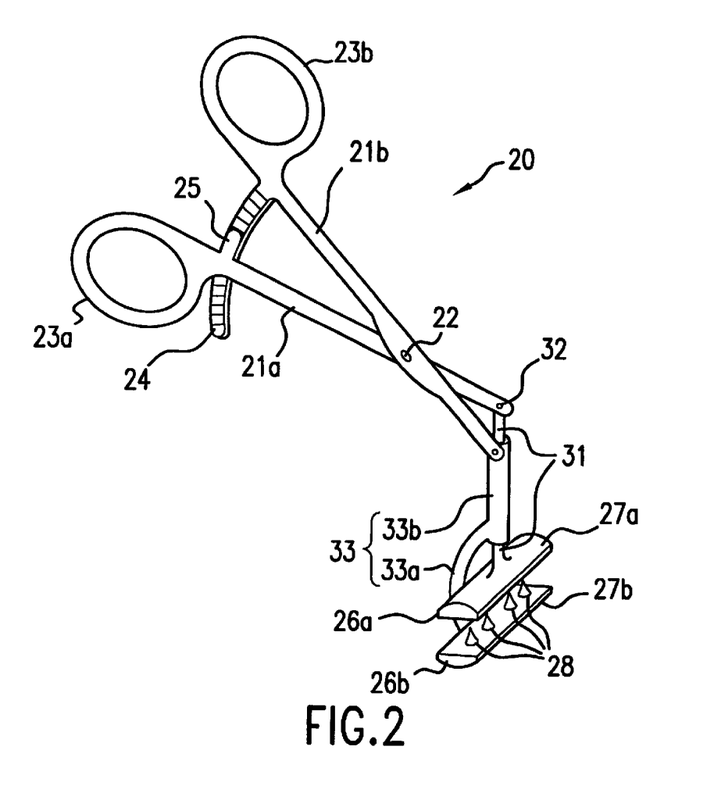
FIG. 2 is a perspective view of a bone clamp in accordance with another embodiment of the present invention utilizing perpendicular structure.

In a manner analogous to that of the previously described embodiment, bone clamp 20 includes a pair of scissor arms 21a and 21b connected through a scissor pivot 22, each including finger loops 23a and 23b provided at respective ends of scissor arms 21a and 21b for receiving hand movement. Bone clamp 20 is depicted in an open position, and is closed by moving finger loops 23a and 23b together by applied hand pressure. Bone clamp 20 also includes a ratchet arc 24 extending from one of the scissor arms 21a and 21b which interacts with a ratchet cog 25, for providing a means for retaining a degree of stepwise closure of clamp 20, the mechanism thereby functioning in a manner analogous with the embodiment of FIG. 1. A pair of jaws 26a and 26b are provided in accordance with the guidelines set forth in accordance with embodiment of the invention, and include, for example as shown in FIG. 2, support structure in the form of support bars 27a and 27b on which gripping structure, conveniently in the form of spaced apart spikes 28, is provided on both (spikes 28 on support bar 27a of upper jaw 26a opposed to spikes 28 on lower jaw 26b not being visible in FIG. 2). Upper jaw 26a is connected to scissor arm 21a via a slidable clamp member 31 which is pivotably connected at a terminal end of scissor arm 21 a conveniently by means of a mounting pivot 32 extending crosswise therethrough. Lower jaw 26b is connected to scissor arm 21b via a tubular clamp member 33 which is pivotably connected at a terminal end of scissor arm 21b. Tubular clamp member 33 includes a hooked jaw support portion 33a integral with or fixedly attached to a free end of a tubular portion 33b through which slidable clamp member 31 is received for slidable travel responsive to movement of scissor arms 21a and 21b. Because tubular portion 33b serves as a guide track for slidable motion of slidable clamp member 31, there advantageously should not be excessive play between the outer diameter of slidable clamp member 31 and the inner diameter of tubular portion 33b, nor should the fit be too snug that smooth sliding motion is impeded.

Each of the aforementioned bone clamps are operated by inserting a thumb and an opposing finger of the same hand through respective finger loops 3a and 3b (or 23a and 23b) and closing scissor arms 1a and 1b (or 21a and 21b) by moving the fingers of the hand together. Depending upon a particular jaw configuration, the bone clamp in accordance with the invention can provide either dynamic or non-dynamic compression of a reduced transverse fracture. In non-dynamic compression, the bone segments are simply maintained in an aligned and abutted orientation to facilitate mending by subsequent procedures. Dynamic compression further involves application of axially applied pressure between the union, a technique which is thought to hasten the healing process and improve recovery. In accordance with a further embodiment of the invention, such dynamic compression is accomplished by virtue of modified gripping structure which creates such axial compression attendant use of the bone clamp, and which compression is subsequently maintained even after the clamp is removed once the bone segments are attached using a desired subsequent fixation procedure prior to such clamp removal.

Embodiments of the invention directed to non-dynamic compression are now described with reference to FIGS. 3–7.

Figure 3:
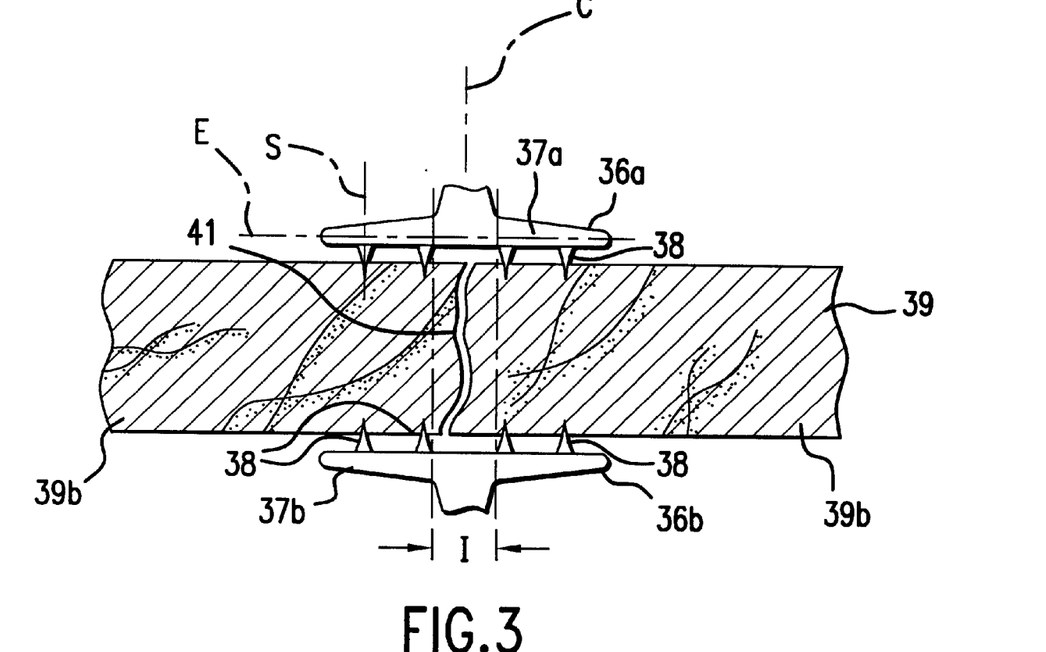
FIG. 3 is a schematic view illustrating operation of a bone clamp for providing non-dynamic compression.

Turning now to FIG. 3, the operation and general construction of a bone clamp jaw for providing non-dynamic compression is depicted, upper and lower jaws being designated 36a and 36b, respectively. Jaws 36a and 36b include support structure which may be provided in any number of suitable forms, and which is provided for illustrative purposes in the depicted example as support bars 37a and 37b. Gripping structure, which may also be provided in a number of suitable forms is provided in the example in the form of spikes 38. As depicted, each jaw 36a or 36b includes two spikes for contacting and/or penetrating into corresponding bone segments 39a and 39b lying on either side of a fracture 41. However, the distribution of spikes need not be symmetrical nor limited to the number as shown. For example, only a single spike may be provided on each jaw for engaging each bone segment 39a and 39b. Similarly, each jaw need not be identical to an opposed jaw. For example, upper jaw 36a may only have two spikes, i.e. one for each bone segment 39a and 39b, and lower jaw 36b provided with two pair of spikes 38 as depicted in FIG. 3.

During a clamping operation, bone 39 is interposed between confronting upper and lower jaws 36a and 36b, advantageously positioned such that transverse fracture line 41 lies within an intermediate region of the expanded dimension of jaws 36a and 36b between ends thereof. In the depicted example of FIG. 3, intermediate region, designated I, is located between adjacent regions of gripping structure (spikes 38) corresponding to engagement with respective bone segments 39a and 39b. Advantageously, gripping structure is omitted within intermediate region I such that a possibly weakened region of bone directly adjacent to the fracture line 41 is not subjected to undue stresses during clamping thereof by jaws 36a and 36b. In such advantageous embodiment, the width of intermediate region I free of gripping structure in a particular practical embodiment will depend upon the nature of the application to which the clamp is directed. Furthermore, notwithstanding the optional separation of gripping structure on either side of the expanded dimension of jaws 36a and 36b by intermediate region I, such gripping structure advantageously extends over a jaw distance sufficient to provide stable clamping if a bone interposed therebetween.

In a bone clamp in accordance with the invention which does not provide dynamic compression, operating on the principles as described in the above embodiment, alternative to the depicted spikes configuration, the gripping structure may comprise a roughened contact surface, one or a series of ridges or other projections for making single or multiple point contact, teeth, and any other configuration, combination of structures and/or material characteristic which achieves a frictional grip when brought into contact with a bone interposed between opposed upper and lower jaws of the bone clamp. It is furthermore noted, that such gripping structure can be designed to merely contact the surface of the bone, or alternatively configured to actually pierce the surface thereof when sufficient hand pressure is applied to the bone clamp, for example, as shown in FIG. 3 in which ends of sharpened spikes 38 penetrate into a bone 39 to further enhance fixation of the bone segments 39a and 39b when clamped in a reduced position as shown for more reliable prevention of movement. It is noted, that in order to prevent axial shifting of bone segments 39a and 39b during piercing thereof in a bone clamp not designed to provide dynamic compression, the penetrating bodies, i.e. spikes 38 or other suitably shaped pointed structure, advantageously presents a cross-sectional shape which is bilaterally symmetric relative a plane S lying approximately parallel to a compression axis C representative of a direction of jaw movement during application of compressive forces on bone 39.

FIGS. 4–7 depict several possible jaw configurations, and serve to illustrate the diversity of design which may be implemented within the scope of the claimed invention. Many other suitable configurations not depicted are also contemplated, as will be apparent to those skilled in the art.

Figure 4:
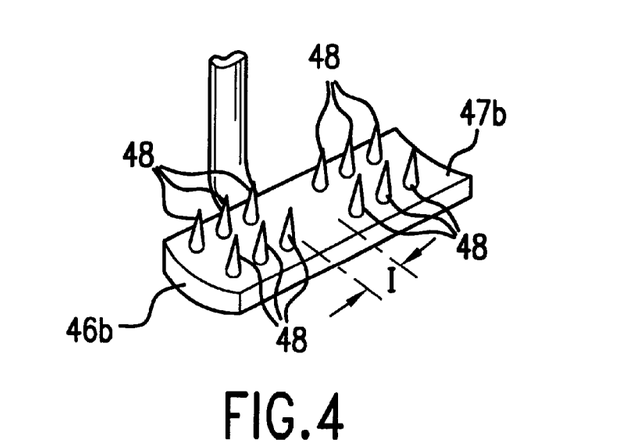
FIG. 4 is a partial perspective front view of a jaw structure for use in a bone clamp for applying non-dynamic compression in reduction and securement of a transverse fracture in accordance with an embodiment of the invention.

FIG. 4 shows a bottom jaw 47b (depiction of a corresponding top jaw of like structure being omitted) which includes support structure provided conveniently in the form of a support plate 47 having a curved surface configuration for matching a generally cylindrical bone shape. Multiple rows (two or more) of spikes 48 are arranged in the axial direction of the expanded dimension of jaw 47 (two rows being depicted in FIG. 4). Spacing between spikes 48 is advantageously wider in intermediate region I than in adjacent gripping regions in order to give the user of the clamp employing such jaw structure greater latitude in positioning a fracture line therebetween.

Figure 5:
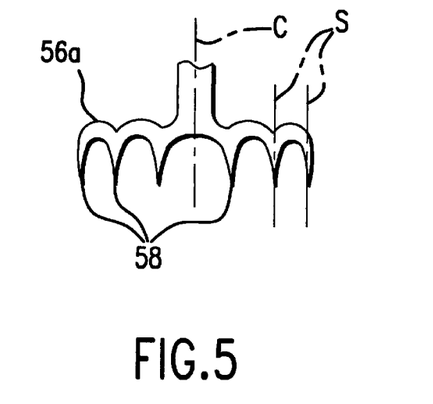
FIG. 5 is a partial perspective front view of an alternative embodiment of a jaw structure for use in a bone clamp for applying non-dynamic compression during an open reduction of a transverse fracture.

The upper jaw structure depicted in FIG. 5, generally designated 56a, is comprised of support structure which, rather than taking the form of a support plate as in the previously described embodiments, is provided as interconnecting structure extending between adjacent spikes 58. As previously noted, since the depicted jaw 56a is directed to non-dynamic fixation, spikes 58 each advantageously presents a cross-sectional shape which is bilaterally symmetric relative plane S lying approximately parallel to compression axis C.

Figure 6:
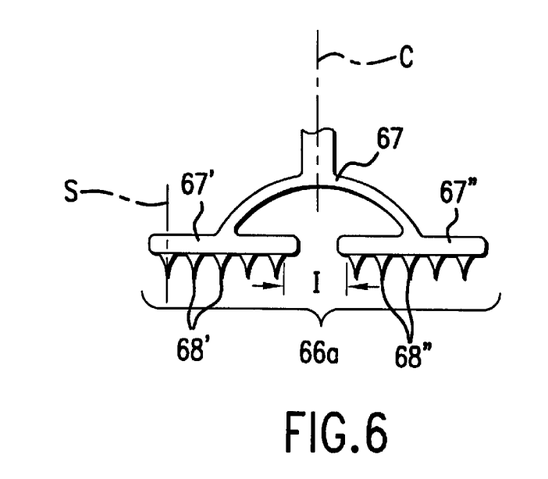
FIG. 6 is a partial perspective front view of a further embodiment of a jaw structure for use in a bone clamp for applying non-dynamic compression during an open reduction of a transverse fracture.

FIG. 6 is illustrative of the principle that the jaw support structure need not extend in a continuous path between gripping regions adapted for contacting respective bone segments separated by a transverse fracture. As shown, an upper jaw 66 includes support structure collectively defined by a separated pair of support plates 67' and 67" and by bifurcated support arms 67 which maintains support plates 66' and 67" in fixed, spaced apart relation. Each of the pair of support plates 67' and 67" presents gripping structure, shown conveniently in the form of spikes 68' and 68" dedicated to engaging corresponding bone segments lying on either side of a transverse fracture line. As with any of the embodiments described herein, other alternative gripping structure may be employed in place of spikes 68' and 68'.

Figure 7:
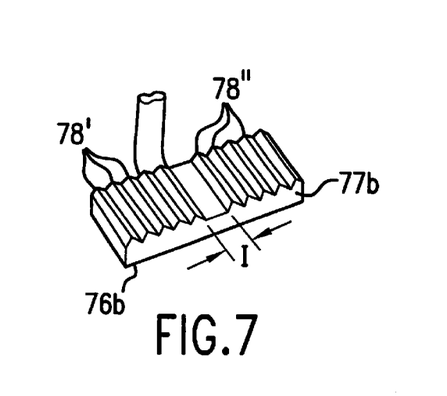
FIG. 7 is a partial perspective front view of another alternative embodiment of a jaw structure for use in a bone clamp for applying non-dynamic compression during an open reduction of a transverse fracture.

Turning now to FIG. 7, a jaw structure includes opposed upper and lower jaws (only lower jaw 76 being shown), each including support structure in the form of a support plate 77b, on which are carried two groups containing a series of toothed ridges 78' and 78', each group for engaging a corresponding bone segment separated by a transverse fracture. Ridges 78' and 78" either fictionally engage an exterior of the bone, or minimally penetrate, to achieve sufficient gripping effect.

Figure 8:
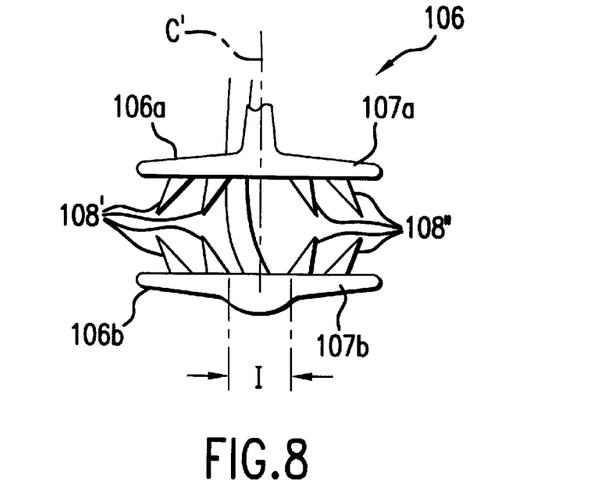
FIG. 8 is a perspective front view of a jaw structure for use in a bone clamp for applying dynamic compression in reduction and securement of a transverse fracture.
Figure 9A:
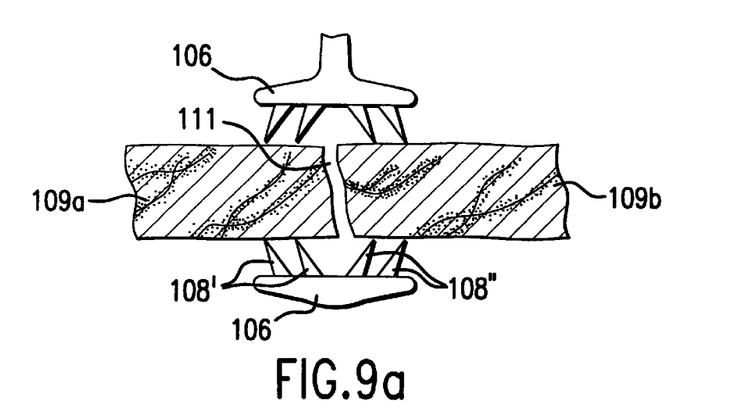
FIG. 9a is an operational schematic front elevational view shown in partial cross-section in which a bone clamp for dynamic compression of a partially reduced fracture is shown in initial engaged contact with adjacent bone segments separated by a transverse fracture.
Figure 9B:
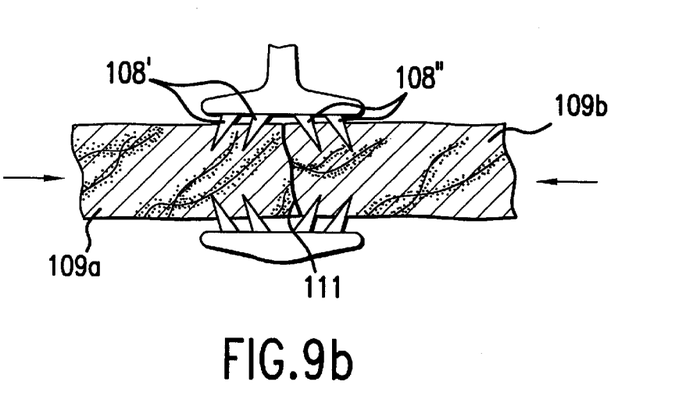
FIG. 9b is an operational schematic front elevational view shown in partial cross-section in which the bone clamp for dynamic compression of FIG. 9b is shown after application of additional pressure illustrating dynamic compression of the fracture.

In a particularly advantageous embodiment of the invention, a jaw structure permits dynamic compression of a transverse fracture by effecting further urging together of bone segments following open reduction thereof and prior to subsequent fixation thereof in a desired method in accordance with acceptable medical practice. Referring now to FIG. 8, a pair of jaws illustrating an example of a structure configuration effecting dynamic compression attendant a clamping operation on reduced bone segments is depicted, the pair of jaws generally designated 106. Jaws 106 include an upper and lower jaw 106a and 106b, respectively, including support structure, conveniently in the form of support plates 107a and 107b. Piercing structure, conveniently in the form of one or more spikes 108' and 108" are laterally disposed on either side of intermediate region I on each jaw 106a and 106b (two being shown in the depicted example) for penetrating corresponding bone segments separated by a transverse fracture, the operation of which is depicted in FIGS. 9a and 9b and for which a description with reference to follows. Spikes 108' and 108" are disposed at an angle outwardly divergent from a compression axis C' representative of a direction of jaw movement effected by closure of jaws 106 during a clamping operation, spikes 108' and 108" being respectively angled away from a transverse fracture line in a direction along a longitudinal axis of a bone interposed between jaws 106. Advantageously, when multiple spikes are provided, the angles at which each of the respective groupings of spikes diverge are approximately equal.

During use of the above described dynamic compression clamp, bone segments 109a and 109b are reduced, bringing them into approximate alignment in which only a small gap exists between a fracture line 111, as shown in FIG. 9a. The aligned bone segments 109a and 109b are interposed between jaws 106, which are urged together by operation of the particular clamp structure on which they are carried, bringing spikes 108' and 108" into initial contact each with a respective one of bone segments 109a and 109b on either side of fracture line 111. Continued urging of jaws 106 together causes spikes 108' and 108" to penetrate bone segments 109a and 109b, as shown in FIG. 9b. Spikes 108' and 108" enter at opposed angles with respect to fracture line 111, continued movement deeper into bone segments 109a and 109b thereby driving bone segments together in the axial direction thereof as indicated by the arrows shown in FIG. 9b. When clamping is complete, bone segments 109a and 109b are temporarily immobilized and the gap between fracture line 111 is concomitantly further reduced, advantageously creating axial compression on the abutted surfaces of the fracture. Such axial compression is maintained following removal of the clamp by fixation of bone segments while clamped using accepted techniques such as by use of interosseous wires, K-wires, plates, screws, etc., as preferred by the surgeon.

The above described non-dynamic and dynamic bone clamp structures differ in principle only with respect to the gripping structure employed. It is importantly noted that all jaw support structures described with regard to non-dynamic jaw structure arrangements can be embodied in analogous fashion with equally efficacious results in jaw structures directed to dynamic compression of transverse fractures, and such design parody is contemplated to be within the intended scope of the invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A bone clamp for temporary securement of adjacent bone segments of an involved bone separated by a fracture following open reduction thereof, said bone clamp comprising:

a pair of jaw members opposed to one another and mutually urgeable together, each of said pair of jaw members including support structure, said support structure presenting an expanded dimension extending between opposed ends thereof, said support structure being oriented crosswise to a direction in which said jaws are urgeable together for codirectional alignment of said expanded dimension with a longitudinal direction of the involved bone when same is received between said pair of jaws, the fracture being oriented proximate an intermediate position located between said opposed ends of the support structure and spaced apart therefrom;

gripping structure carried on said support structure in a gripping region between each of said opposed ends and either corresponding side of said intermediate position of both of said pair of jaws for opposed contact of said gripping structure of each said gripping region with a respective one of the adjacent bone segments, said gripping structure being brought into secured engagement by continued urging together of said pair of jaws;

said gripping structure including penetrating bodies at least a portion of which at least partially pierce said involved bone in response to continued urging together of said pair of jaws;

said penetrating bodies including at least two spikes carried on each of said pair of jaw members, at least one of said at least two spikes being disposed on each side of said intermediate position on each of said pair of jaw members; and said at least two spikes are disposed one on each side of said intermediate position, each of said at least two spikes being oriented at an angle outwardly divergent from a compression axis extending through said intermediate position and which is representative of a direction of jaw movement effected by urging together of closure of said pair of jaws and codirectionally angled with respect to said expanded direction, said at least two spikes thereby being respectively angled away from the fracture in a direction along a longitudinal axis of the involved bone interposed between said pair of jaws whereby continued urging of said pair of jaws effects reduction of the fracture.

2. A bone clamp according to claim 1, further comprising:

hand-operable structure for transmitting and converting manually applied force into motion selectively effecting urging together of said pair of jaws and subsequent separation thereof.

3. A bone clamp according to claim 1, wherein said penetrating bodies present a cross-sectional shape which is bilaterally symmetric relative a plane lying crosswise said expanded direction and approximately parallel to a compression axis representative of a direction of jaw movement during application of compressive forces on said involved bone.

4. A bone clamp according to claim 1, wherein said support structure includes a support plate having a curved surface configuration for matching a generally cylindrical shape of the involved bone.

5. A bone clamp according to claim 1, wherein said at least two spikes include at least four spikes, a spacing of said at least four spikes being wider in a region extending about said intermediate position than in each said gripping region adjacent thereto.

6. A bone clamp according to claim 1, wherein said at least two spikes include spikes arranged in groupings on opposite sides of said intermediate position, angles at which spikes in respective groupings diverge being approximately equal.

7. A bone clamp according to claim 1, further comprising hand-operable structure for transmitting and converting manually applied force into motion selectively effecting urging together of said pair of jaws and subsequent separation thereof.

8. A bone clamp according to claim 7, wherein said mechanism includes a ratchet.

9. A method of temporarily securing adjacent bone segments of an involved bone separated by a fracture, the method comprising:

providing a clamp including a pair of jaw members opposed to one another and mutually urgeable together, each of said pair of jaw members including support structure, said support structure presenting an expanded dimension extending between opposed ends thereof and carrying gripping structure in respective gripping regions each located between one of said opposed ends and a corresponding side of an intermediate position located between said opposed ends of the support structure and spaced apart therefrom, said gripping structure including penetrating bodies for at least partially piercing the adjacent bone segments, said piercing bodies comprising at least two spikes carried on each of said pair of jaw members, at least one of said at least two spikes being disposed on each side of said intermediate position on each of said pair of jaw members;

orienting the involved bone between said pair of jaws with the fracture located within an intermediate region extending about said intermediate position;

urging said pair of jaws together such that said gripping structure of each of said respective gripping regions is brought into mutual pressurized contact with a respective one of the adjacent bone segments to permit subsequent repair of the bone segments thereby held in place following reduction thereof;

said at least two spikes being disposed one on each side of said intermediate position, each of said at least two spikes being oriented at an angle outwardly divergent from a compression axis extending through said intermediate position and which is representative of a direction of jaw movement effected by urging together of closure of said pair of jaws and codirectionally angled with respect to said expanded direction, said at least two spikes thereby being respectively angled away from the fracture in a direction along a longitudinal axis of the involved bone interposed between said pair of jaws; and said step of urging being continued to effect the reduction of the fracture by penetration of respective ones of said spikes into corresponding ones of the adjacent bone segments.

\* \* \* \* \*